United States Patent [19]

Smith

[11] Patent Number: 5,206,248
[45] Date of Patent: Apr. 27, 1993

[54] METHOD FOR REDUCING EMOTIONAL LABILITY

[76] Inventor: Richard A. Smith, 7569 Cabrillo Ave., La Jolla, Calif. 92037

[21] Appl. No.: 859,105

[22] Filed: Mar. 27, 1992

[51] Int. Cl.$^5$ .............................................. A61K 31/44
[52] U.S. Cl. ................................... 514/289; 514/282; 514/305
[58] Field of Search ......................... 514/289, 305, 282

[56] References Cited

PUBLICATIONS

N. H. Kalin et al, "Opiate modulation of separation-induced distress in non-human primates," *Brain Research* 440: 285–292 (1988).

M. D. Nielsen et al, "A dose-effect study of the in vivo inhibitory effects of quinidine . . ." *Br. J. Clin Pharmac.* 29: 299–304 (1990).

F. Broly et al, "Inhibitory studies of mexiletine and dextromethorphan oxidation . . ." *Biochem. Pharmacology* 39: 1045–1052 (1990).

CA 108: 124860y, Kalin et al., 1988.

CA 112: 171691m, Due Nielsen et al., 1990.

CA 112: 210493v, Broly et al., 1990.

*Primary Examiner*—Frederick E. Waddell
*Assistant Examiner*—Kimberly R. Jordan
*Attorney, Agent, or Firm*—Patrick D. Kelly

[57] ABSTRACT

This invention discloses that certain types of non-addictive opioid drugs such as dextromethorphan (which is widely used in cough syrups) provide a highly effective means of treating the feelings and symptoms of emotional lability in at least some patients suffering from neurologic impairment, without sedating, tranquilizing, or otherwise significantly interfering with consciousness or alertness in the patient. In several patients tested to date who were suffering from amyotrophic lateral sclerosis (ALS), dextromethorphan, administered orally, was remarkably effective and became quite obvious to the patients even though it was being tested for an entirely different purpose. Its effectiveness is enhanced by co-administration of a second drug such as quinidine which reduces the degradation of dextromethorphan by oxidative enzymes and which therefore increases dextromethorphan concentrations in the blood.

15 Claims, No Drawings

METHOD FOR REDUCING EMOTIONAL LABILITY

BACKGROUND OF THE INVENTION

This invention is in the field of neuropharmacology, and relates to methods of treating patients suffering from emotional problems that occur in relation to neurodegenerative diseases or to brain damage such as caused by stroke or head injury.

The phrase "emotional lability" is used by psychiatrists and neurologists to refer to a set of symptoms that are often observed in patients who have suffered a brain insult such as a head injury, stroke, brain tumor, or encephalitis, or who are suffering from a progressive neurodegenerative disease such as amyotrophic lateral sclerosis (ALS, also called motor neuron disease or Lou Gehrig's disease), Parkinson's disease, Alzheimer's disease, or multiple sclerosis. In the great majority of such cases, emotional lability occurs in patients who have bilateral damage (i.e., damage which affects both hemispheres of the brain) involving subcortical forebrain structures.

Emotional lability, which is distinct from clinical forms of reactive or endogenous depression, is characterized by intermittent spasmodic outbursts of emotion (usually manifested as intense or even explosive crying or laughing) at inappropriate times or in the absence of any particular provocation. The feelings that accompany emotional lability are often described in words such as "disconnectedness," since patients are fully aware that an outburst is not appropriate in a particular situation, but they do not have control over their emotional displays. Emotional lability is also described by some as "emotional incontinence," which draws an analogy between someone who is unable to control emotional outbursts, and someone who is unable to control their bladder or bowels.

Emotional lability becomes a clinical problem when the inability to control emotional outbursts interferes in a substantial way with the ability to engage in family, personal, or business affairs. For example, a businessman suffering from early-stage ALS or Parkinson's disease might become unable to sit through business meetings, or a patient might become unable to go out in public, such as to a restaurant or movie, due to transient but intense inability to keep from crying or laughing at inappropriate times in front of other people. These symptoms can occur even though the patient still has more than enough energy and stamina to do the physical tasks necessary to interact with other people. Such outbursts, along with the feelings of annoyance, inadequacy, and confusion that they usually generate and the visible effects they have on other people, can severely aggravate the other symptoms of the disease; they lead to feelings of ostracism, alienation, and isolation, and they can render it very difficult for friends and family members to provide tolerant and caring emotional support for the patient. Accordingly, emotional lability needs to be regarded as a distinct symptom that causes considerable suffering, and an effective method of treating it would be very helpful to sufferers and their families.

The best previously known therapies for treating emotional lability involve the drugs amitriptyline, amantadine, and levodopa. Although reports such as Udaka et al 1984 and Schiffer et al 1985 (complete citations are provided below, before the claims) indicate that these compounds may be effective in helping reduce pathological displays of emotion in some patients, they make it clear that none of these prior art drugs are effective in all patients, and even in patients who receive some benefit, the effect usually stops far short of an effective cure. A common practice for many clinical neurologists is to prescribe amitriptyline and amantadine, one at a time, in the hope that one of them might be able to provide any level of improvement in the patient's condition. However, all both fall short of offering an effective cure. In addition, levodopa is not satisfactory, since it has other effects and is a relatively powerful drug.

Accordingly, there remains a need for additional or improved forms of treatment for emotional lability. Such a treatment should provide, at a minimum, at least some degree of improvement compared to other known drugs, in at least some patients.

In fact, the treatment described herein has provided a truly remarkable and outstanding level of improvement in a number of the patients tested to date. This improvement was so beneficial and so clear that it quickly became apparent and came to the forefront as a primary effect of the treatment, even though the treatment was being evaluated for an entirely different purpose.

One object of this invention is to provide a method for treating emotional lability in at least some patients suffering from neurologic impairment, such as a progressive neurologic disease.

Another object of this invention is to disclose that dextromethorphan, which is known to selectively block activity at the NMDA class of glutamate receptors in the central nervous system (CNS) and which has some utility in protecting CNS neurons against death or damage due to certain toxic processes, has been discovered to have a separate and distinct beneficial effect: it is highly effective in reducing the external symptoms and the internal feelings of emotional lability in at least some patients who, prior to treatment, were suffering from an inability to control inappropriate emotional outbursts.

SUMMARY OF THE INVENTION

This invention discloses that certain types of non-addictive opioid drugs such as dextromethorphan (which is widely used in cough syrups) provide a highly effective means of treating the feelings and symptoms of emotional lability in at least some patients suffering from neurologic impairment, without sedating, tranquilizing, or otherwise significantly interfering with consciousness or alertness in the patient. In several patients tested to date who were suffering from amyotrophic lateral sclerosis (ALS), dextromethorphan, administered orally, was remarkably effective and became quite obvious to the patients even though it was being tested for an entirely different purpose. Its effectiveness is enhanced by co-administration of a second drug such as quinidine which reduces the degradation of dextromethorphan by oxidative enzymes and which therefore increases dextromethorphan concentrations in the blood.

DETAILED DESCRIPTION OF THE PREFERRED EMBODIMENTS

This invention discloses a method of treating emotional lability (i.e., uncontrollable and frequently inappropriate displays of emotion) in human patients who are in need of such treatment, without sedating, tranquilizing, or otherwise significantly interfering with consciousness or alertness in the patient. The treatment involves a non-addictive opioid which can penetrate the blood-brain barrier, such as dextromethorphan.

Dextromethorphan is widely used as a cough syrup, and it has been shown to be sufficiently safe in humans to allow its use as an over-the-counter medicine in cough syrups. It is well tolerated in oral dosage, either alone or with quinidine (as discussed below), at up to 120 milligrams (mg) per day. At least one patient noticed a beneficial effect when receiving a substantially smaller dose (30 mg/day).

The chemistry of dextromethorphan and its analogs is described in various references such as Rodd 1960, Goodman and Gilman's *Pharmacological Basis of Theraoeutics*, Choi 1987, and U.S. Pat. No. 4,806,543 (Choi 1989). Its chemical structure is as follows:

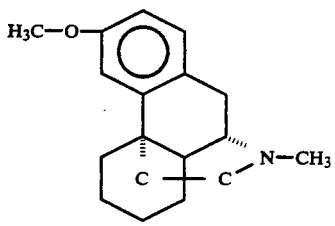

Dextromethorphan (frequently abbreviated as DM) is the common name for (+)-3-methoxy-N-methylmorphinan. It is one particular molecule from a class of molecules which are dextrorotatory analogs of morphine-like opioids. The term "opiate" refers to drugs that are derived from opium (from the poppy plant) such as morphine and codeine. The term "opioid" is broader; it includes opiates, but it also includes other drugs, natural or synthetic, which act as analgesics or sedatives in mammals.

Most of the addictive analgesic opiates, such as morphine, codeine, and heroin, are levorotatory stereoisomers (i.e., they will rotate polarized light in the so-called left-handed direction). They have four molecular rings in a configuration known as a "morphinan" structure, which is depicted as follows:

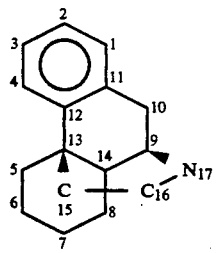

In this depiction, the carbon atoms are conventionally numbered as shown, and the wedge-shaped bonds coupled to carbon atoms 9 and 13 indicate that those bonds rise out of the plane (toward a reader who is looking at the page) of the three other rings in the morphinan structure. Many important analogs of this basic structure (including morphine) are pentacyclic compounds that have an additional ring formed by a bridging atom (such as oxygen) between the number 4 and 5 carbon atoms.

Many dextrorotatory analogs of morphine are much less addictive than the levorotatory compounds. Some of these dextrorotatory analogs, including dextromethorphan and dextrorphan, are "enantiomers" (mirror images) of the morphinan structure. In these enantiomers, the ring that extends out from carbon atoms 9 and 13 is oriented in the opposite direction (away from the reader, in the structural depiction of dextromethorphan shown above, as indicated by the dotted-line bonds).

One of the significant characteristics of the treatment disclosed herein is that it functions to reduce emotional lability without sedating, tranquilizing, or otherwise significantly interfering with consciousness or alertness in the patient. As used herein, "significant interference" refers to adverse effects that would be significant either on a clinical level (e.g., they would provoke a specific concern in a doctor or psychologist) or on a personal or social level (e.g., such as by causing drowsiness sufficiently severe that it would impair someone's ability to drive an automobile). By contrast, the type of very minor side effects that might be caused by an over-the-counter drug such as a dextromethorphan-containing cough syrup when used at recommended dosages are not regarded as significant interference.

Receptor Activities

The following discussion relating to the receptor activities of dextromethorphan is not intended to limit the scope of the invention, which is based on a useful and practical observation of a highly beneficial effect in human patients during clinical trials. Nevertheless, this discussion is offered in order to provide information on the probable molecular mechanisms involved in those beneficial effects, and to provide useful information which will indicate which analogs of dextromethorphan are preferred candidates for screening tests to evaluate their ability to confer similar or perhaps even better results in other human patients.

Dextromethorphan is known to have at least three distinct receptor activities which affect CNS neurons.

First, it acts as an antagonist at NMDA receptors, i.e., it blocks or suppresses activity at N-methyl-D-aspartate receptors. NMDA receptors are one of three major types of "excitatory amino acid" (EAA) receptors in CNS neurons. Since activation of NMDA receptors causes neurons to release excitatory neurotransmitter molecules (primarily glutamate, an amino acid), the blocking activity of dextromethorphan at these receptors reduces the level of excitatory activity in neurons having those receptors. Dextromethorphan is believed to act at the phencyclidine (PCP) binding site, which is part of the NMDA receptor complex. It should be noted that dextromethorphan is relatively weak in its NMDA antagonist activity, particularly compared to drugs such as MK-801 (dizocilpine) and phencyclidine. Accordingly, when administered at approved dosages, dextromethorphan is not believed to cause the toxic side effects (discussed in U.S. Pat. No. 5,034,400, Olney 1991) that are caused by powerful NMDA antagonists such as MK-801 or PCP.

Second, dextromethorphan also functions as an agonist (it triggers activity) at certain types of inhibitory receptors; unlike EAA receptors, activation of inhibitory receptors suppresses the release of excitatory neurotransmitters by affected cells. Initially, these inhibitory receptors were called sigma opiate receptors; however, questions were raised about whether they are actually opiate receptors, so neurologists began simply calling them sigma ($\sigma$) receptors.

Subsequently, additional experiments showed that dextromethorphan also binds to another class of inhibitory receptors that are closely related to, but distinct from, sigma receptors. The evidence which indicates that non-sigma inhibitory receptors exist and are being bound by dextromethorphan is that certain molecules which bind to sigma receptors are not able to completely block the binding of dextromethorphan to certain types of neurons that are known to have inhibitory receptors (see Craviso and Musacchio 1983, Musacchio 1988, and Klein et al 1989). These receptors are usually called "high-affinity dextromethorphan receptors" or simply as "DM receptors" in the scientific literature. As used herein, the phrase "dextromethorphan-binding inhibitory receptors" includes both sigma and non-sigma receptors which undergo affinity-binding reactions with dextromethorphan and which, when activated by dextromethorphan, suppress the release of excitatory neurotransmitters by the affected cells. For more information on such receptors, see Klein et al 1989, Craviso and Musacchio 1983, Largent 1987, and Musacchio et al 1988.

Third, dextromethorphan also decreases the uptake of calcium ions ($Ca^{++}$) by neurons. Calcium uptake, which occurs during transmission of nerve impulses, involves at least two different types of channels, known as N-channels and L-channels. Dextromethorphan suppressed calcium uptake fairly strongly in certain types of cultured neurons (synaptosomes) which contain N-channels; it also suppressed calcium uptake, although less strongly, in other cultured neurons (PC12 cells) which contain L-channels (Carpenter et al 1988).

The highly complex interactions between different types of neurons having varying populations of different receptors, and the cross-affinity of different receptor types for dextromethorphan as well as other types of molecules which can interact with some or all of those same types of receptors, render it very difficult to attribute the overall effects of dextromethorphan to binding activity at any particular receptor type. Nevertheless, it is clear that dextromethorphan suppresses neuronal activity by means of at least three molecular functions: (1) it reduces activity at (excitatory) NMDA receptors; (2) it inhibits neuronal activity by binding to certain types of inhibitory receptors; and (3) it suppresses calcium uptake through N-channels and L-channels.

It is clear, from the results observed by the Applicant, that dextromethorphan provides a practical, non-addictive treatment for emotional lability, and this treatment has been far more effective than any prior art treatments in a number of patients studied to date. Although these observations may trigger research to further study and quantify the contributions by each receptor type, the productive therapeutic use of this treatment by patients who need help in controlling emotional lability does not have to wait for that type of analysis.

It should also be noted that, unlike some analogs of morphine, dextromethorphan has little or no agonist or antagonist activity at various other opiate receptors, including the mu ($\mu$) or kappa ($\kappa$) classes of opiate receptors. This is highly desirable, since agonist or antagonist activity at those opiate receptors can cause undesired side effects such as respiratory depression (which interferes with breathing) or blockade of analgesia (which reduces the effectiveness of pain-killers).

Accordingly, one of the teachings of this invention is that emotional lability can be treated in at least some patients by means of administering a drug to the patients in need of such treatment, wherein the drug functions as an antagonist at NMDA receptors and as an agonist at dextromethorphan-binding inhibitory receptors, and wherein the drug is also characterized by a lack of agonist or antagonist activity at mu or kappa opiate receptors.

Analogs of Dextromethorphan

The effects of a drug on the central nervous system depend, not on the exact chemical structure of the drug, but on the activity of the drug at receptors on the surfaces of neurons. This is particularly true of a drug such as dextromethorphan, which is merely one specific molecule in a heavily-studied class of drugs that are known to include numerous analogs. For example, in the analog dextrorphan (which is generated as a metabolite in people who take dextromethorphan), the methoxy group coupled to the number 3 carbon atom of dextromethorphan is replaced by a hydroxy group. The relevant properties of dextrorphan are quite similar to dextromethorphan; both are cough suppressants which have little or no detectable addictive, analgesic, or narcotic side effects. Both compounds are agonists at sigma receptors, and antagonists at NMDA receptors.

Accordingly, dextrorphan and various other analogs of dextromethorphan can be screened as described below, using no more than routine experimentation, to determine whether they will exert the same beneficial effects shown by dextromethorphan in treating emotional lability. In order to be useful for the purposes described herein, a suitable dextromethorphan analog must have at least the following characteristics:

1. it must be suited for oral administration;
2. it must be able to penetrate the mammalian blood-brain barrier in a sufficient quantity to exert a therapeutic effect inside the brain; and,
3. it must not display substantial addictive or narcotic properties in humans.

Analogs which are dextrorotatory are preferred for screening as described herein, since they are likely to be less addictive and to have fewer side effects than levorotatory analogs. In addition, analogs which have significant activity as both sigma agonists and NMDA antagonists, as can be determined in cell culture tests, are preferred for screening in human patients, since such analogs are more likely to closely duplicate or resemble the overall beneficial effects and activities of dextromethorphan which occur in the central nervous systems of patients suffering from emotional lability.

Screening tests to evaluate the effects of any non-addictive analog of dextromethorphan in humans can be performed by administering any such analog, on a trial basis, to patients who have been diagnosed by a neurologist or psychiatrist as suffering from clinically cognizable emotional lability. A recommended testing protocol would begin at a relatively mild dosage such as about 30 mg/day and would last for a period such as one month; as discussed below, the initial concentration should be further reduced if the analog is administered in conjunction with a second agent which increases blood plasma concentrations. Patients would be fully informed in advance and must give informed and voluntary consent. They should be asked to report on whether their internal feelings and/or external symptoms improved during the trial period, using either a numerical scale (such as 0 to 10) or a set of descriptive phrases (such as "Extremely poor" to "Exceptionally good")." If satisfactory results are not reported by the patient at the end of the trial period, the dosage can increasing in increments of 30 mg/day, up to about 120 mg/day, or possibly higher if a specific patient shows no adverse effects at that dosage and if the doctor deems it advisable to try a higher dosage.

Due to variations in the enzymatic pathways that metabolize dextromethorphan (discussed below), it is anticipated that certain analogs of dextromethorphan may work more effectively in some patients, while other patients may report better results for different analogs.

Co-Administration with Compounds that Prolong Activity

It has long been known that in most people (estimated to include about 90% of the general population in the United States), dextromethorphan is rapidly metabolized and eliminated by the body; see, e.g., Ramachander 1977 and Vettican 1989. This elimination is largely due to an enzyme known as the P450-2D6 (or IID6) enzyme, which is one member of a class of oxidative enzymes that exist in high concentrations in the liver, known as cytochrome P450 enzymes (Kronbach et al 1987; Dayer et al 1989). In addition to metabolizing dextromethorphan, the P450-2D6 isozyme also oxidizes sparteine and debrisoquine.

It is known in the prior art that the P450-2D6 enzyme can be inhibited by a number of drugs, particularly quinidine (Brinn et al 1986; Inaba et al 1986; Brosen et al 1987; Otton et al 1988; Funck-Brentano et al 1989; Nielsen et al 1990; Broly et al 1989).

Patients who lack the normal levels of P450-2D6 activity are classified in the medical literature as "poor metabolizers," and doctors are generally warned to be cautious about administering various drugs to such patients; in the words of Guttendorf et al 1988, "The diminished oxidative biotransformation of these compounds in the poor metabolizer (PM) population can lead to excessive drug accumulation, increased peak drug levels, or in some cases, decreased generation of active metabolites . . . Patients with the PM phenotype are at increased risk of potentially serious untoward effects . . . " (page 490). Accordingly, doctors must be cautious about administering quinidine to patients, and rather than using drugs such as quinidine to inhibit the rapid elimination of DM, researchers working in this field have administered very large quantities (such as 750 mg/day) of dextromethorphan to their patients, even though this is known to introduce various problems (e.g., Walker and Hunt 1989; Albers 1991).

However, the Applicant took a rather different approach. To determine whether the problems of rapid DM elimination could be overcome, the Applicant decided to assess the effects of co-administration of quinidine along with dextromethorphan, in ALS patients. In addition to trying to increase the levels of circulating dextromethorphan in the blood, this research was also designed to evaluate whether the enzymatic pathways involved in DM degradation were altered, compared to humans who do not have ALS.

In the first round of tests, which were designed to provide baseline values, DM was administered (at escalating doses, starting at 30 mg/day and increasing up to 120 mg/day) to ALS patients without co-administration of quinidine, and concentrations of DM in blood plasma were measured. They were found to be very low, except in one patient who was also taking the anti-depressant drug Prozac (fluoxetine), which is known to suppress at least some cytochrome P-450 oxidative enzymes (see, e.g., Shen and Lin 1991).

In the second round of tests, quinidine was administered orally at 150 mg per day. The 150 mg/day dosage was well below the dose normally used to treat cardiac arrhythmias (typically 600 to 1200 mg/day). Quinidine was also tested at 300 mg/day with no adverse effects; since it was found to be effective at 150 mg/day, the lower dosage was selected. Dextromethorphan was administered twice daily. When quinidine administration began, the DM dosage was restarted at the lowest level which had previously been tested (30 mg/day); if no adverse effects were observed, the dosage was increased in a step-wise fashion.

The quinidine administration greatly increased DM concentrations in the blood plasma. For example, in the absence of quinidine, 120 mg of DM per day resulted in plasma concentrations of $12\pm13$ nanograms of DM per ml of blood plasma (the values ranged from undetectable levels (less than 5 ng/ml) to 40 ng/ml). By contrast, in the presence of quinidine, the same dosage of DM resulted in plasma concentrations of $241\pm94$ ng/ml (range 157 to 402 ng/ml).

One patient suffered a severe adverse reaction at the 30 mg/day dosage of DM, when quinidine was co-administered. He had not previously suffered any adverse reaction when DM alone was administered. His reaction, which lasted several days, was similar to the hallucinatory and psychotic reactions that are often observed in people who illegally abuse the drug phencyclidine (also known as PCP or "angel dust"). PCP is a powerful NMDA antagonist, and DM is a relatively weak NMDA antagonist. That individual had also reported abnormalities in responding to codeine. It is not known whether those abnormalities were due to unusual receptor sensitivities, variations in the enzymes that metabolize drugs such as DM or codeine, or other factors.

Based on that observation and other precautionary comments in the *Physician's Desk Reference* (PDR), it is recommended that if quinidine (or any other drug which is known to suppress oxidative enzymes) is to be co-administered to a patient along with dextromethorphan or an analog thereof, the quinidine should be administered all by itself for an initial period, under the guidance of a physician, to ensure that the patient is not hypersensitive or allergic to the quinidine or other agent. In addition, the warnings in the PDR should be taken into account in determining whether quinidine poses a likely risk to a patient having a condition such as a liver or kidney ailment, or to a patient taking any other drug which might interact with either quinidine or DM. If the patient is not hypersensitive or allergic to quinidine or another selected oxidation inhibitor, then the initial dosage of DM should be restricted to about 10 mg/day for at least a week while the patient is monitored for hypersensitivity to the combination.

Except for the one patient who was hypersensitive and one other patient who had what appeared to be an allergic reaction to quinidine administered alone, no other patients tested by the Applicant suffered any significant adverse reactions from co-administration of quinidine with dextromethorphan. Quinidine co-administration was shown to have at least two distinct beneficial effects. First, it greatly increased the quantities of DM which were circulating in the blood, which led to the observation that dextromethorphan has a remarkable and highly beneficial effect in controlling emotional lability.

In addition, it also led to more consistent and predictable DM concentrations. Humans are known to vary substantially in their oxidative metabolism. For example, about 7-10% of the people in the U.S. have very low rates of dextromethorphan metabolism, which suggests that are missing, or have abnormally low quantities of, the P450-2D6 isozyme. It can be very difficult to evaluate the effects of drugs such as DM during research projects, if the drugs being studied are metabolized quite differently by different people. Administration of a conjunctive agent such as quinidine can reduce those differences, thereby allowing a higher level of predictability and comparability during evaluative research.

The research involving co-administration of quinidine and dextromethorphan, and the effects of quinidine on blood plasma concentrations, is described in more detail in U.S. patent application Ser. No. 717,424, which designates the same inventor as the subject application and which is hereby incorporated by reference.

In the first round of tests involving dextromethorphan without quinidine, none of the patients being tested volunteered any comments indicating that their emotional state had been significantly altered during the trial period. The patients were not asked about their emotional condition as part of the evaluation, since DM was being tested solely to evaluate whether it helped slow down the physical symptoms of ALS.

However, in subsequent tests which included quinidine, the ability of several patients to control their emotional lability was so marked and noticeable that it became apparent to the Applicant, a neurologist who was treating the patients.

Since quinidine is not known to have any receptor activity or direct psychoactive effects inside the CNS, it is believed that the same or similar results could be achieved without requiring co-administration of quinidine, by increasing the dosage of dextromethorphan to very high levels (as are being used by other research teams). The question of whether quinidine has any direct effect on emotional lability will be evaluated during control tests as the effects of dextromethorphan are evaluated further; one of the control populations will contain patients who will receive quinidine but not dextromethorphan.

Dextromethorphan concentrations in the blood can also be increased by administering any of numerous other drugs which inhibit the oxidative activity of cytochrome P450 enzymes (particularly drugs which specifically inhibit the P450-2D6 isozyme). Numerous such drugs are known to exist; see, e.g., Inaba et al 1985, in which the suppression of sparteine oxidation correlates with P450-2D6 activity. Some of these drugs have other effects which can be valuable in their own right, including antidepressants such as fluoxetine (the common name for N-methyl-gamma-[4-(trifluoromethyl)phenoxy]benzenepropanamine, sold under the trademark Prozac), certain beta-adrenoceptor blocking drugs and other cardiovascular drugs which are administered to heart patients, and various antihistamines or plant-derived alkaloids. Such drugs may be preferable to quinidine in patients who are being simultaneously treated for conditions other than emotional lability, in patients who suffer PCP-like reactions or other adverse reactions indicating hypersensitivity to DM in the presence of quinidine, and/or in patients who are sensitive to quinidine by itself. Any such drug can be screened using routine experimantation to determine whether it is effective in increasing the blood plasma concentration of dextromethorphan, or of any analog or derivative of dextromethorphan which is being tested for beneficial effect in controlling emotional lability as described herein. Any patient being tested with any such combination of drugs should be monitored for adverse effects that might be due to the combination, and any such test should begin with low doses of both drugs.

Treatment of Other Types of Emotional Lability

The discovery that dextromethorphan can reduce the internal feelings and external symptoms of emotional lability in some patients suffering from progressive neurological disease suggests that dextromethorphan is also likely to be useful for helping some patients suffering from emotional lability due to other causes, such as stroke or other ischemic (low blood flow) or hypoxic (low oxygen supply) events which led to neuronal death or damage in limited regions of the brain, or head injury or trauma as might occur during an automobile, motorcycle, or bicycling accident or due to a gunshot wound.

In addition, the results obtained to date also suggest that dextromethorphan is likely to be useful for treating some cases of emotional lability which are due to administration of other drugs. For example, various steroids such as prednisone are widely used to help treat autoimmune diseases such as lupus; however, prednisone has adverse effects on the emotional states of many patients, ranging from mild but noticeably increased levels of moodiness and depression, up to severely aggravated levels of emotional lability that can impair the business, family, or personal affairs of the patient.

In addition, dextromethorphan (preferably with a second agent that slows down DM oxidation) is a promising candidate and will be evaluated to determine whether it can reduce the external displays or the internal feelings that are caused by or which accompany various other problems such as "premenstrual syndrome" (PMS), Tourette's syndrome, and the outburst displays that occur in people suffering from certain types of mental illness. Although such problems may not be clinically regarded as emotional lability, they involve manifestations that appear to be sufficiently similar to emotional lability to suggest that dextromethorphan may offer an effective treatment for at least some patients suffering from such problems. The effectiveness of such treatment for any individual suffering from any such problem can be assessed on a routine basis by means of a simple trial which involves administering DM (preferably in conjunction with an agent which increases DM concentrations in the blood) to the patient for a trial period, asking the patient to report on whether his or her internal feelings or external manifestations seemed to improve during the trial period, and, if desired, having neurologists, counselors, or family members evaluate the patient to determine whether a noticeable improvement has occurred. If the dextromethorphan causes a substantial improvement, its administration can be continued.

A recommended trial protocol involves an initial trial involving quinidine alone, followed by one week at a relatively low dosage such as 10 mg DM and 100 to 150 mg quinidine per day, taken orally, to determine whether the patient is hypersensitive to the combination. If the patient is not hypersensitive, the DM dosage can be increased to 30, 60, 90, and 120 mg/day, for a period of one month at each dosage.

EXAMPLES

All patients discussed below were diagnosed as suffering from ALS. They consented to participate in a test to determine whether dextromethorphan might be able to slow down the progression of the disease; this treatment test was intended to evaluate a hypothesis which suggests that excitotoxicity might play a role in neuronal death in ALS patients. The patients were initially tested for dosage tolerance, beginning with a 30 mg/day oral dosage which lasted one week and which was increasing on a weekly basis, up to 120 mg/day if adverse symptoms were not observed.

During the initial stages of the dextromethorphan test, before the benefits of suppression of emotional lability had been noticed by anyone, it was recognized that blood concentrations of dextromethorphan were very low or undetectable in all patients except one, who was also taking Prozac (fluoxetine). A literature search revealed that fluoxetine tends to suppress the oxidative activity of the cytochrome P-450 class of liver enzymes (see, e.g., Shen and Lin 1991). It was recognized that suppression of that oxidative activity might be responsible for increasing the blood concentrations of dextromethorphan, so a second literature search was undertaken to evaluate other drugs which had the same oxidation-suppression activity without the psychoactive activity of Prozac. This search revealed that quinidine is a highly effective inhibitor of one particular type of cytochrome oxidase activity, which involves the oxidation of sparteine monooxygenase by one particular isozyme in the P-450 class of enzymes (Inaba et al 1985). Even though quinidine had no effect whatever in inhibiting other isozymes, it was selected for an experimental trial which involved co-administration in the dextromethorphan trials.

All patients described below took the oral dosage of quinidine (150 mg) each morning along with half of their daily dosage of dextromethorphan. Twelve hours later, they took the rest of their dextromethorphan dosage.

EXAMPLE 1

Patient MM, a 72 year old male who had worked as a farmer, experienced some falls and difficulty walking. He told his physician, and upon being referred to the Applicant (a neurologist), the patient was diagnosed as having ALS. During discussions with the Applicant, the patient had fits of crying characteristic of emotional lability, and he complained of similar occurrences at other times; as one example, during a Christmas holiday, he attempted to give a gift (a family possession he had owned for many years) to one of his grandsons, but was totally overcome with crying and feelings of grief and could not give the gift.

The patient subsequently enrolled in a one-month experimental trial using dextromethorphan as a treatment for possible excitotoxic damage which might be occurring in ALS. While the dextromethorphan was being administered, the continuing physical decline characteristic of ALS (e.g., continued loss of muscle strength, fatigue, shortness of breath, etc.) was not helped in any detectable way. However, the patient noticed a dramatic change in his rapid mood swings; he no longer broke into tears during discussions with the neurologist, and he reported that his emotional state had greatly stabilized. He even managed to give a comparable gift to another grandson with no difficulty whatever. An improvement was noticeable at 30 mg/day. The patient continues to take dextromethorphan, at a daily dosage of 90 mg/day.

EXAMPLE 2

Patient WM, a 58 year old male businessman, began to notice difficulty with his speech and loss of emotional control. He would become tearful at the slightest provocation, even during business meetings, to the point where it was disrupting his work and his relations with coworkers. Thinking he might have had a stroke, he consulted a physician, and was instead diagnosed with ALS. Subsequently, he enrolled in an experimental trial using dextromethorphan; while receiving 60 mg/day, his blood plasma concentrations usually averaged between 43 and 55 nanograms per milliliter. Although his physical symptoms did not improved, his problems with unexpected bouts of tearfulness, in his words, "just faded away" and the patient was able to return to work with an emotional state that he regarded as normal. Dextromethorphan is currently being administered at 120 mg/day.

EXAMPLE 3

Patient BK, a 67 year old male, noticed leg weakness and muscle cramping. He consulted a neurologist and was diagnosed as having ALS. Along with his neuromuscular complaints, the patient reported that he frequently breaks into tears with little or no outside provocation.

The patient subsequently participated in an experimental trial using dextromethorphan, and settled in at a 90 mg/day dosage (blood plasma levels usually averaged between 130 and 180 ng/ml). Since it was not helping his physical symptoms, he stopped taking it when the trial period ended. However, when he stopped taking it, his emotional state worsened, and he realized that while taking dextromethorphan, he had felt calmer and emotionally normal. When he reported those symptoms to the Applicant, the Applicant prescribed dextromethorphan again at 90 mg/day. Once again, the patient's emotional state improved and stabilized. When the dextromethorphan was discontinued a second time, the patient's emotional instability returned again, and he again reported that he would break into tears for no apparent reason.

Thus, there has been shown and described an improved method for treating emotional lability. It will be apparent to those skilled in the art that various changes and modifications to the specific embodiments described herein are possible. Any such changes that do not depart from the spirit and scope of the invention are deemed to be covered by the invention, which is limited only by the claims which follow.

REFERENCES

Albers, G. W., et al, "Safety and tolerance of oral dextromethorphan in patients at risk for brain ischemia," *Stroke* 22: 1075–1077 (1991)

Brinn, R., et al, "Sparteine oxidation is practically abolished in quinidine-treated patients," *Br. J. Clin. Pharmacol.* 22: 194–197 (1986)

Broly, F., et al, "Effect of quinidine on the dextromethorphan O-methylase activity of microsomal fractions from human liver," *Br. J. Clin. Pharmacol.* 28: 29–36 (1989)

Brosen, K., et al, "Extensive metabolizers of debrisoquine become poor metabolizers during quinidine treatment," *Pharmacol. Toxicol.* 60: 312-314 (1987)

Carpenter, C. L., et al, "Dextromethorphan and dextrorphan as calcium channel antagonists," *Brain Research* 439: 372-375 (1988)

Choi, D. W., "Dextrorphan and dextromethorphan attenuate utamate neurotoxicity," *Brain Res.* 403: 333-336 (1987)

Craviso, G. L., and Musacchio, J. M., "High affinity dextromethorphan binding sites in guinea pig brain," *Mol. Pharmacol.* 23: 619-640 (1983)

Dayer, R., et al, "Dextromethorphan O-demethylation in liver microsomes..." *Clin. Pharmacol. Ther.* 45: 34-40 (1989)

Guttendorf, R. J., et al, "Simplified phenotyping with dextromethorphan by thin-layer chromatography: Application to clinical laboratory screening for deficiencies in oxidative drug metabolism," *Ther. Druo. Monit.* 10: 490-498 (1988)

Inaba, T., et al, "Quinidine: Potent inhibition of sparteine and debrisoquine oxidation in vivo," *Br. J. Clin. Pharmacol.* 22: 199-200 (1986)

Klein, M., et al, "The effects of prototypic sigma ligands on the binding of [$^3$H] dextromethormethorphan to guinea pig brane, " *Neuroscience Letters* 97: 175-180 (1989)

Kronbach, T., et al, "High performance liquid chromatographic assays... purified cytochrome P-450 isozymes of human liver," *Anal. Biochem.* 162: 24-32 (1987)

Largent, B. L., et al, "Structural determinants of sigma receptor affinity," *Mol. pharmacol.* 32: 772-784 (1987)

Musacchio, J. M., et al, "High affinity dextromethorphan binding sites in the guinea pig brain," *J. Pharmacol. Exp. Ther.* 247: 424-431 (1988)

Nielsen, M. D., et al, et al, "A dose-effect study of the in vivo inhibitory effect of quinidine on sparteine oxidation in man," *Br. J. Clin. Pharmacol.* 29: 299-304 (1990)

Otton, S. V., et al, "In vitro evidence against the oxidation of quinidine by the sparteine.debrisoquine monooxygenase of human liver," *Drug Metab. Diso.* 16: 15-17 (1988)

Ramachander, G., et al, "Determination of dextrorphan in plasma and evaluation of bioavialability dextromethorph hydrobromide in humans," *J. Pharm. Sci.* 66: 1047-1048 (1977)

Rodd, E. H., ed., *Chemistry of Carbon Compounds* (Elsevier Publ., N.Y., 1960)

Schiffer, R. B., et al, "Treatment of pathological laughing and weeping with amitriptyline," *N. Engl. J. Med.* 312: 1480-1482 (1985)

Udaka, T., et al, "Pathological laughing and crying treated with levodopa," *Arch. Neurol.* 41: 1095-1096 (1984)

Vettican, S. J., et al, "Phenotypic differences in dextromethorphan metabolism," *Pharmaceut. Res.* 6: 13-19 (1989)

Walker, F. O. and Hunt, V. P., "An open-label trial of dextromethorphan in HUntington's disease," *Clin. Neuropharm.* 12: 322-330 (1989)

I claim:

1. A method for reducing emotional lability in human patients, comprising orally administering, to a patient in need thereof, a therapeutically effective quantity of non-addictive analog of morphine which penetrates a mammalian blood-brain barrier, and which causes a reduction in spasmodic outbursts of emotion without significantly interfering with consciousness or alertness in the patient.

2. The method of claim 1 wherein the non-addictive analog of morphine is a dextrorotatory enantiomer of an analgesic morphinan.

3. The method of claim 2 wherein the non-addictive analog of morphine is selected from the group consisting of dextromethorphan and dextrorphan.

4. The method of claim 1 wherein the non-addictive analog of morphine is co-administered with a second compound which inhibits oxidative degradation of the non-addictive analog of morphine.

5. The method of claim 1 wherein the second compound which inhibits oxidative degradation of the non-addictive analog of morphine comprises quinidine.

6. A method for reducing emotional lability in humans, comprising the oral administration to a patient in need thereof a therapeutically effective quantity of a non-addictive analog of morphine which penetrates mammalian blood-brain barriers and which reacts with dextromethorphan-binding receptors, thereby suppressing the release or excitatory neurotransmitters by neurons containing such receptors, wherein the non-addictive analog of morphine causes a reduction in spasmodic outbursts of emotion without significantly interfering with consciousness or alertness in the patient.

7. The method of claim 6 wherein the non-addictive analog of morphine is a dextrorotatory enantiomer of an analgesic morphinan.

8. The method of claim 6 wherein the non-addictive analog of morphine is selected from the group consisting of dextromethorphan and dextrorphan.

9. The method of claim 6 wherein the non-addictive analog of morphine is co-administered with a second compound which inhibits oxidative degradation of the non-addictive analog of morphine.

10. The method of claim 6 wherein the second compound which inhibits oxidative degradation of the non-addictive analog of morphine comprises quinidine.

11. A method for reducing inappropriate displays of emotion, comprising a oral administration, to a patient suffering from inappropriate emotional outbursts, of a therapeutically effective quantity of non-addictive analog of morphine which penetrates mammalian blood-brain barriers and which reacts with dextromethorphan-binding receptors, thereby suppressing the release of excitatory neurotransmitters by neurons containing such receptors, wherein the non-addictive analog of morphine causes a reduction in outbursts of emotion without significantly interfering with consciousness or alertness in the patient.

12. The method of claim 11 wherein the non-addictive analog of morphine is a dextrorotatory enantiomer of an analgesic morphinan.

13. The method of claim 11 wherein the non-addictive analog of morphine is selected from the group consisting of dextromethorphan and dextrorphan.

14. The method of claim 11 wherein the non-addictive analog of morphine is co-administered with a second compound which inhibits oxidative degradation of the non-addictive analog of morphine.

15. The method of claim 11 wherein the second compound which inhibits oxidative degradation of the non-addictive analog of morphine comprises quinidine.

* * * * *